United States Patent [19]
Essen-Moller

[11] Patent Number: 5,479,935
[45] Date of Patent: Jan. 2, 1996

[54] AMBULATORY REFLUX MONITORING SYSTEM

[75] Inventor: Anders Essen-Moller, Stockholm, Sweden

[73] Assignee: Synectics Medical, Inc., Irving, Tex.

[21] Appl. No.: 139,117

[22] Filed: Oct. 21, 1993

[51] Int. Cl.[6] ........................................ A61B 5/05
[52] U.S. Cl. ............................. 128/734; 128/780
[58] Field of Search ........................ 128/632, 634, 128/635, 734, 642, 733, 780

[56] References Cited

U.S. PATENT DOCUMENTS

| | | |
|---|---|---|
| 2,162,656 | 6/1939 | Warrington . |
| 2,168,867 | 8/1939 | George, 3rd . |
| 2,857,915 | 10/1958 | Sheridan . |
| 3,373,735 | 3/1968 | Gallagher . |
| 3,480,003 | 11/1969 | Crites . |
| 3,669,095 | 6/1972 | Kobayashi et al. . |

(List continued on next page.)

FOREIGN PATENT DOCUMENTS

| | | |
|---|---|---|
| 0073558 | 3/1983 | European Pat. Off. . |
| 0080680 | 6/1983 | European Pat. Off. . |
| 2453630 | 11/1980 | Germany . |
| 3140265 | 4/1983 | Germany . |
| 221635 | 5/1985 | Germany . |
| 7707275 | 1/1979 | Netherlands . |
| 178028 | 11/1966 | U.S.S.R. . |
| 272477 | 5/1968 | U.S.S.R. . |
| 1502004 | 8/1989 | U.S.S.R. . |

OTHER PUBLICATIONS

"Clinical relevance of ambulatory 24-hour . . . ", Vogten, et al., 1987, pp. 21–31 in Netherlands Journal of Medicine.
"Computerized Axial Manometry of the Esophagus", Bombeck, et al. in Annals of Surgery, vol. 206, No. 4, pp. 465–472, Oct. 1987.
"The laser motility sensor for long–term study of intraesophageal pressure", Schneider et al., in Primary Motility Disorder of the Esophagus, Giuli et al., eds. pp. 64–69 1991.
Kim et al., American Journal of Clinical Pathology, 1990, vol. 94, pp. 187–191, "The Gastric Juice Urea and Ammonia . . . ".
Butcher et al., Digestion, 1992, vol. 53, pp. 142–148, "Use of an Ammonia Electrode for Rapid Quantification of *Helicobacter pylori* Urease: Its use in the Endoscopy Room and in the . . . ".
The New Yorker, Sep. 20, 1993, T. Monmaney, "Marhsall's Hunch".
"Oesophageal multipurpose monitoring probe", Baker et al., Anaesthesia, 1983, vol. 38, pp. 892–897.
Digestive Diseases, Reprint, vol. 8, Suppl. 1, pp. 60–70, 1990, Scarpignato et al., "Simultaneous Measurement and Recording . . . ".
Hojgaard et al., "A New Method for Measurement of the Electrical Potential Difference Across the Stomach Wall", 1991. pp. 847–858.
"Ambulatory Monitoring of Gastric Emptying", Hoeft et al., May 16, 1993, American Assoc. of the Study of Live Diseases.

*Primary Examiner*—Max Hindenburg
*Attorney, Agent, or Firm*—Stephen C. Glazier

[57] ABSTRACT

An ambulatory system for recording and analyzing gastroesophageal reflux is presented. The system comprises a digital recorder, an analysis software package and a catheter for measurement of changes in esophageal impedance. For the first time, gastroesophageal reflux can be detected with a pH above 4 (called alkaline reflux), which is the normal pH environment of the healthy esophagus. In addition, one embodiment of the invention allows for the determination of the direction of flow of the detected material in the esophagus, thus enabling the system to distinguish between swallowed saliva and alkaline gastroesophageal reflux. In yet a further embodiment, the present invention allows for recording and analysis of reflux on a non-invasive basis, by using pairs of externally worn impedance sensors. In another embodiment, the invention measures impedance simultaneously with other bio-parameters, such as pH or pressure.

10 Claims, 3 Drawing Sheets

U.S. PATENT DOCUMENTS

| | | | |
|---|---|---|---|
| 3,690,309 | 9/1972 | Pluzhnikov et al. | |
| 3,817,241 | 6/1974 | Grausz. | |
| 3,905,889 | 9/1975 | Macur et al. | |
| 3,923,626 | 12/1975 | Niedrach et al. | |
| 4,016,866 | 4/1977 | Lawton. | |
| 4,063,548 | 12/1977 | Klatt et al. | |
| 4,073,287 | 2/1978 | Bradley et al. | |
| 4,119,498 | 10/1978 | Edwall et al. | 204/11 |
| 4,176,659 | 12/1979 | Rolfe | 128/635 |
| 4,197,852 | 4/1980 | Schindler et al. | 128/635 |
| 4,208,588 | 6/1980 | Rudin | 250/496 |
| 4,214,593 | 7/1980 | Imbruce et al. | 128/748 |
| 4,265,249 | 5/1981 | Schindler et al. | 128/635 |
| 4,299,929 | 11/1981 | Sakano et al. | 525/67 |
| 4,381,011 | 4/1983 | Somers, 3rd | 128/635 |
| 4,442,841 | 4/1984 | Uehara et al. | 128/635 |
| 4,471,779 | 9/1984 | Antoshkiw et al. | 128/325 |
| 4,476,871 | 10/1984 | Hon | 128/642 |
| 4,478,222 | 10/1984 | Koning et al. | 128/632 |
| 4,486,290 | 12/1984 | Cahalan et al. | 128/635 |
| 4,487,206 | 12/1984 | Aagard | 128/667 |
| 4,503,859 | 3/1985 | Petty et al. | 128/635 |
| 4,508,103 | 4/1985 | Calisi | 128/673 |
| 4,577,640 | 3/1986 | Hofmeister | 128/738 |
| 4,593,701 | 6/1986 | Kobayashi et al. | 128/667 |
| 4,600,015 | 7/1986 | Evans et al. | 128/780 |
| 4,618,929 | 10/1986 | Miller et al. | 364/415 |
| 4,631,061 | 12/1986 | Martin | 604/318 |
| 4,632,119 | 12/1986 | Reichstein | 128/632 |
| 4,642,104 | 2/1987 | Sakamoto et al. | 604/265 |
| 4,655,225 | 4/1987 | Dahne et al. | 128/633 |
| 4,681,116 | 7/1987 | Settler | 128/635 |
| 4,682,596 | 7/1987 | Bales et al. | |
| 4,691,708 | 9/1987 | Kane | 128/667 |
| 4,696,672 | 9/1987 | Mochizuki et al. | 604/128 |
| 4,700,709 | 10/1987 | Kraig | 128/635 |
| 4,700,799 | 10/1987 | Kawano | 180/219 |
| 4,703,757 | 11/1987 | Cohen | 128/667 |
| 4,705,503 | 11/1987 | Dorman et al. | 604/50 |
| 4,729,384 | 3/1988 | Bazenet | 128/691 |
| 4,748,113 | 5/1988 | Marshall | 435/12 |
| 4,748,562 | 5/1988 | Miller et al. | 364/415 |
| 4,757,194 | 7/1988 | Simms | 250/227 |
| 4,776,347 | 10/1988 | Matthews | 128/774 |
| 4,796,629 | 1/1989 | Grayzel | 128/344 |
| 4,803,992 | 2/1989 | Lemelson | 128/634 |
| 4,815,471 | 3/1989 | Stobie | 128/748 |
| 4,834,101 | 5/1989 | Collison et al. | 128/635 |
| 4,836,214 | 6/1989 | Sramek | 128/734 |
| 4,850,371 | 7/1989 | Broadhurst et al. | 128/719 |
| 4,852,580 | 8/1989 | Wood | 128/734 |
| 4,873,990 | 10/1989 | Holmes et al. | 128/748 |
| 4,887,610 | 12/1989 | Mittal | 128/733 |
| 4,892,101 | 1/1990 | Cheung et al. | 128/633 |
| 4,901,731 | 2/1990 | Millar | 128/675 |
| 4,924,877 | 5/1990 | Brooks | 128/748 |
| 4,966,161 | 10/1990 | Wallace et al. | 128/748 |
| 4,975,581 | 12/1990 | Robinson et al. | 128/633 |
| 4,976,265 | 12/1990 | Falcial et al. | 128/634 |
| 4,981,470 | 1/1991 | Bombeck, IV | 128/635 |
| 4,986,671 | 1/1991 | Sun et al. | 374/131 |
| 4,991,590 | 2/1991 | Shi | 128/667 |
| 4,996,161 | 2/1991 | Conners et al. | 128/719 |
| 5,005,584 | 4/1991 | Little | 128/748 |
| 5,007,427 | 4/1991 | Suzuki et al. | 128/659 |
| 5,018,529 | 5/1991 | Tenerz | 128/667 |
| 5,022,396 | 6/1991 | Watanabe | 128/642 |
| 5,025,786 | 6/1991 | Siegel | 128/642 |
| 5,046,497 | 9/1991 | Millar | 128/637 |
| 5,047,627 | 9/1991 | Yim et al. | 128/634 |
| 5,054,487 | 10/1991 | Clarke | 128/633 |
| 5,103,835 | 4/1992 | Yamada et al. | 128/734 |
| 5,105,812 | 4/1992 | Corman | 128/635 |
| 5,108,364 | 4/1992 | Takezawa et al. | 604/43 |
| 5,109,870 | 5/1992 | Silney et al. | 128/734 |
| 5,117,827 | 6/1992 | Stuebe et al. | 128/635 |
| 5,119,498 | 6/1992 | McNeill et al. | 395/800 |
| 5,151,598 | 9/1992 | Denen | 128/654 |
| 5,158,083 | 10/1992 | Sacristan et al. | 128/635 |
| 5,184,619 | 2/1993 | Austin | 128/639 |
| 5,199,443 | 4/1993 | Maurer et al. | 128/788 |
| 5,207,226 | 5/1993 | Bailin et al. | 128/661.08 |
| 5,222,594 | 6/1993 | Sumino | 198/808 |
| 5,280,786 | 1/1994 | Wlodarczyk et al. | 128/634 |
| 5,291,884 | 3/1994 | Heinemann et al. | 128/633 |
| 5,301,673 | 4/1994 | Rabito et al. | 128/659 |
| 5,314,804 | 5/1994 | Boguslaski et al. | 435/12 |

AMBULATORY REFLUX MONITORING SYSTEM

FIELD OF INVENTION

The present invention is an ambulatory recording and analysis system for use in the gastrointestinal tract. More particularly, the present invention records and analyzes gastro-esophageal reflux. Specifically, this is done by reading and recording changes in esophageal impedance with sensors. This allows recording and analysis of reflux when it is impossible with the prior art, that is when the refluxed material has a pH above 4 (called alkaline reflux). The present invention can be used in both intraesophageal and non-invasive applications.

BACKGROUND

Certain methods and apparatus are known in the prior art for 24 hour monitoring of intraesophageal pH in patients with suspected reflux disease or other esophageal disorders. An example of a system for ambulatory 24 hour recording of gastroesophageal reflux is the Digitrapper™ System (manufactured by Synectics Medical AB, in Stockholm, Sweden) used with glass or Monocrystant™ pH catheters (as described in U.S. Pat. No. 4,119,498) and with the analysis software EsopHogram™ (by Gastrosoft, Inc. in Dallas, Tex.). These prior art systems typically measure pH in the esophageal tract with an intraesophageal catheter and generate reports regarding esophageal exposure of gastric juice. However, these systems measure pH values in the esophagus below 4, and do not work to detect pH values that are higher than 4.

Normally, pH values in the stomach are below 4 and in the esophagus are between 4 and 7. Hence, these prior art systems are designed to detect and measure the presence of gastric juice in the esophagus by measuring esophagus pH below 4. However, gastric juice does at times, and particularly in the early morning, become more alkaline, with a pH above 4. Hence, the prior art systems cannot detect gastroesophageal reflux of gastric juice of this type at these times, with a pH above 4.

Efforts have been made to define and report as reflux rapid changes of intraesophageal pH, while the pH remains within the normal esophageal range of pH, which is between 4 and 7. Such changes, however, can be difficult to prove to be caused by true gastroesophageal reflux, and in some instances may not be caused by reflux.

Others have measured alkaline reflux with radioisotope techniques. With these techniques, a radioisotope is administered to the patient and accumulates in the bile. With a gamma camera sensor placed externally on the patient's chest or internally within the esophagus, it is possible to detect gastroesophageal reflux containing the isotope, regardless of pH. The use of radioactive material and the expense of stationary or ambulatory gamma cameras make the radioisotope method for detection of alkaline reflux unattractive.

Intestinal impedance measurement has previously been used in measurements of gastric emptying into the intestines. In such studies, a liquid or solid meal is administered to a patient and changes in intestinal impedance are monitored from external electrodes around the abdomen. However, the prior art has not taught a system for analyzing gastroesophageal reflux by means of recording changes in esophageal impedance, nor of a system for ambulatory measurement of the same.

Impedance measurements have also been used for monitoring chest movements as a means of monitoring respiration in patients at risk for apnea. Other impedance monitors are used to detect urine leakage in the urethra in urodynamic procedures. Yet other impedance monitors are used for measurement of body fat and for phletysmography.

However, the prior art does not teach using changes in impedance for detection of gastroesophageal reflux, on an ambulatory basis or otherwise.

Since the prior art does not teach how to record and analyze alkaline reflux, it is not surprising that it also does not teach how to distinguish detection of alkaline reflux from detection of swallowed saliva. This is a matter of importance, since alkaline reflux may have a pH and an impedance that is similar to swallowed saliva, which is commonly found in any esophagus.

It is an object with the present invention to provide an ambulatory system that provides the possibility to detect gastroesophageal reflux regardless of its pH value by means of recording and analyzing esophageal impedance. It is a further object with the present invention to provide a system that can detect the direction of flow of matter in the esophagus, thus being able to separate alkaline gastroesophageal reflux from swallowed saliva. It is yet a further object of the present invention to provide presently used intraesophageal pH and pressure catheters with the means to detect gastroesophageal reflux according to the present invention. It is yet a further object with the present invention to provide a system that can be used noninvasively with a number of sensors for impedance measurements placed on and around the chest of the patient for ambulatory recording of reflux.

SUMMARY OF THE INVENTION

An ambulatory system for recording and analyzing gastroesophageal reflux is presented. The system comprises a digital recorder, an analysis software package and a catheter for measurement of changes in esophageal impedance. For the first time, gastroesophageal reflux can be detected with a pH above 4 (called alkaline reflux), which is the normal pH environment of the healthy esophagus. In addition, one embodiment of the invention allows for the determination of the direction of flow of the detected material in the esophagus, thus enabling the system to distinguish between swallowed saliva and alkaline gastroesophageal reflux. In yet a further embodiment, the present invention allows for recording and analysis of reflux on a non-invasive basis, by using pairs of externally worn impedance sensors.

DETAILED DESCRIPTION OF THE PREFERRED EMBODIMENTS

Figure 1:
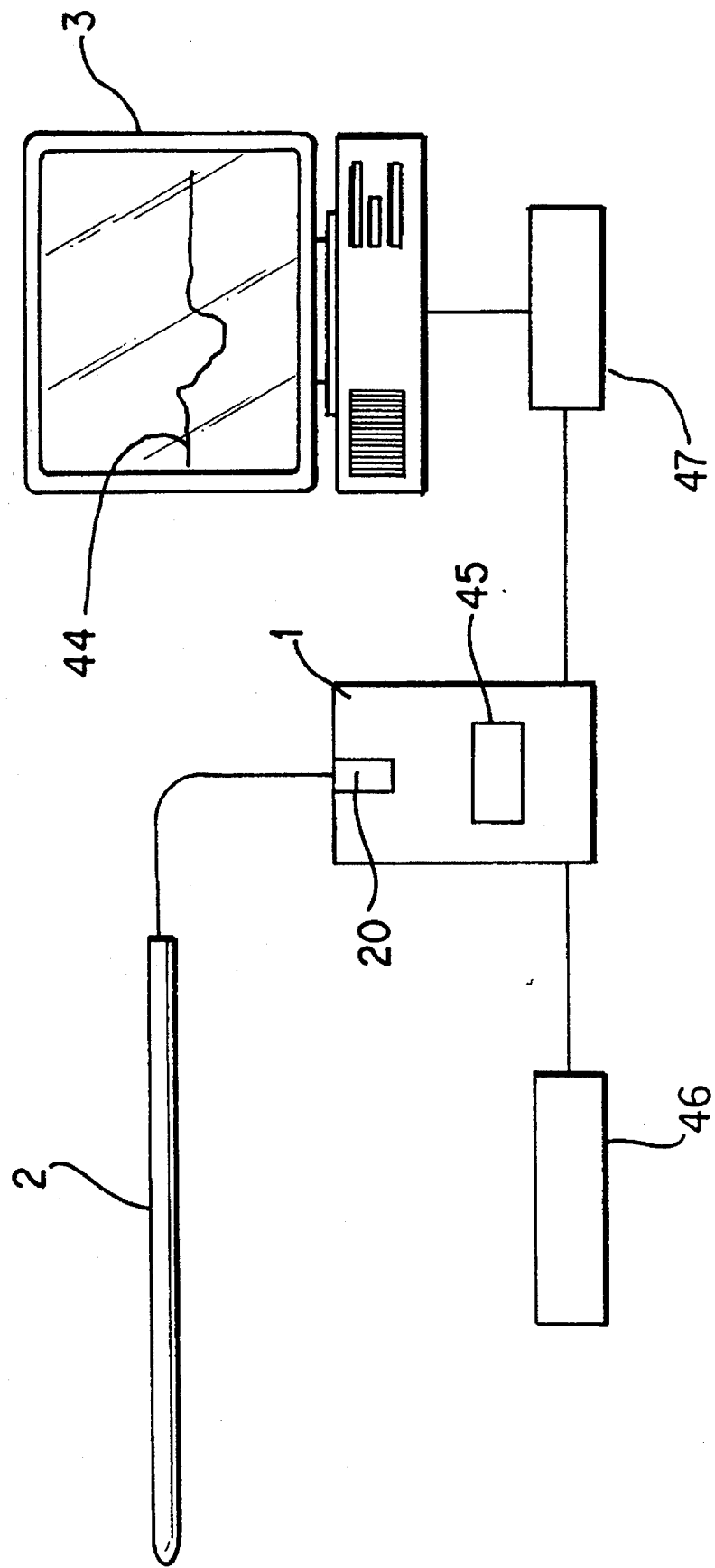
FIG. 1 shows a schematic view of the system of one embodiment of the present invention, and the projected graphic data developed by the system.

FIG. 1 shows an embodiment of the present invention with an ambulatory digital recorder 1 connected to an intraesophageal catheter 2. The recorder can contain software to analyze the data and prepare a graphic projection 44 of the data. The data and analysis can be projected on a display 45 on the recorder, or the recorder can be connected to a printer 46 to print out hard copy of the data, the analysis, and the graphic projection. The hard copy can be used for visual analysis, manual analysis, or otherwise. Also, the recorder may be connected to a modem 47 to communicate the data to a personal computer 3, or the recorder can be connected directly to the personal computer 3. Where a computer is used, software resident in the computer, instead of in the recorder, may be used for analysis of the recorded data. The computer also can print out hard copy for visual graphic analysis, manual analysis, or otherwise, in a manner similar to when the recorder directly communicates to a printer 46.

Figure 2:
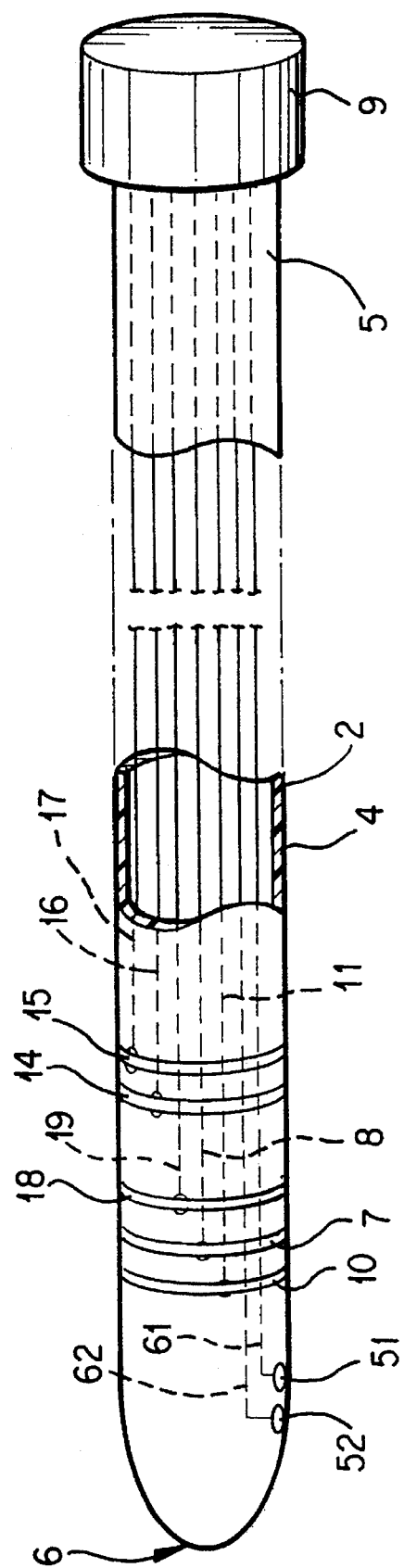
FIG. 2 shows a side view of the catheter of the present invention.

FIG. 2 shows one embodiment of the catheter 2 with tubing 4 made of PVC (poly-vinyl-chloride) with a proximal end 5 and a distal end 6. A first 0.2 mm wide metal ring of gold 7 encloses tubing 4 at a distance 6 cm from distal end 6. A first conducting lead 8 is connected to said metal ring 7 and runs internally inside tubing 4 along the catheter and out through proximal end 5, ending in connector means 9. A second gold ring 10 is positioned 2 mm distal to first ring 7 and a second lead 11 is connected to said second ring and runs inside along tubing 4 out through its proximal end 5, ending in connector means 9. It has been found by the inventor that such close placement of the rings 7 and 10, only 2 mm from each other, provides for more accurate impedance readings than possible when the rings are placed farther apart. Connector means 9 with leads 8 and 11 of catheter 2 is connected to recorder 1. Preamplifier 20 in recorder 1 supply leads 8 and 9 with 50 mV at 1.5 kHz AC. In addition, preamplifier 20 includes means to detect changes in impedance between metal ring 7 and 10. Such changes in impedance occur when gastroesophageal reflux reaches up to the rings.

In another embodiment of catheter 2 of the present invention, an additional set of two metal rings 14 and 15 are placed around the outer surface of catheter 2, spaced 2 mm apart from each other as are rings 7 and 10, and placed 1 cm toward the proximal end of the catheter from ring 10. The additional rings 14 and 15 are connected to leads 16 and 17, respectively, which both run inside catheter 2 to the proximal end 5 of catheter 2, where they end in connector means 9. The additional set of metal rings may be used to measure impedance changes in an additional channel.

By analyzing which pair of rings first show a change in impedance, the direction of flow of the measured material in the esophagus can be determined. This allows distinguishing between a swallow of saliva, which is alkaline and moves down the esophagus, and alkaline gastroesophageal reflux, which moves up the esophagus. When gastric juice breaks the barrier of the lower esophageal sphincter and rises in the esophagus, the change in impedance is first registered between rings 7 and 10 and subsequently between the next set of rings 14 and 15 proximal to, and higher up the esophagus than, the first said set of rings 7 and 10. On the other hand, swallowed saliva moving down the esophagus will first reach the higher set of rings 14 and 15 and will cause a change in impedance between these rings, before a change in impedance between the lower rings 7 and 10 can be seen. It is in this way possible to determine the direction of flow of material in the esophagus. In this way is distinguished gastroesophageal reflux, which moves up the esophagus, from swallowed saliva, which moves down the esophagus, regardless of the pH of either of such materials.

In yet another embodiment of catheter 2, rings 7 and 10 are complemented with only one additional ring 18 placed proximal to ring 7. Said additional ring is connected by lead 19 which runs inside catheter 2 towards the proximal end 5 and to connector means 9. By using ring 7 and 10 on one hand and 7 and 18 on the other hand 2 sets of two rings can be created for independent measurement and confirmation of impedance.

In FIG. 1, preamplifier 20 in recorder 1 supplies catheter 2 with an alternating current of 50 mV at 1.5 kHz to rings 7 and 10 through leads 8 and 11, and to other sets of rings if used. The preamplifier 20 includes means for recording changes in impedance between rings 7 and 10 and between other sets of rings if available. The changes in impedance are measured and stored in recorder 1.

Figure 3:
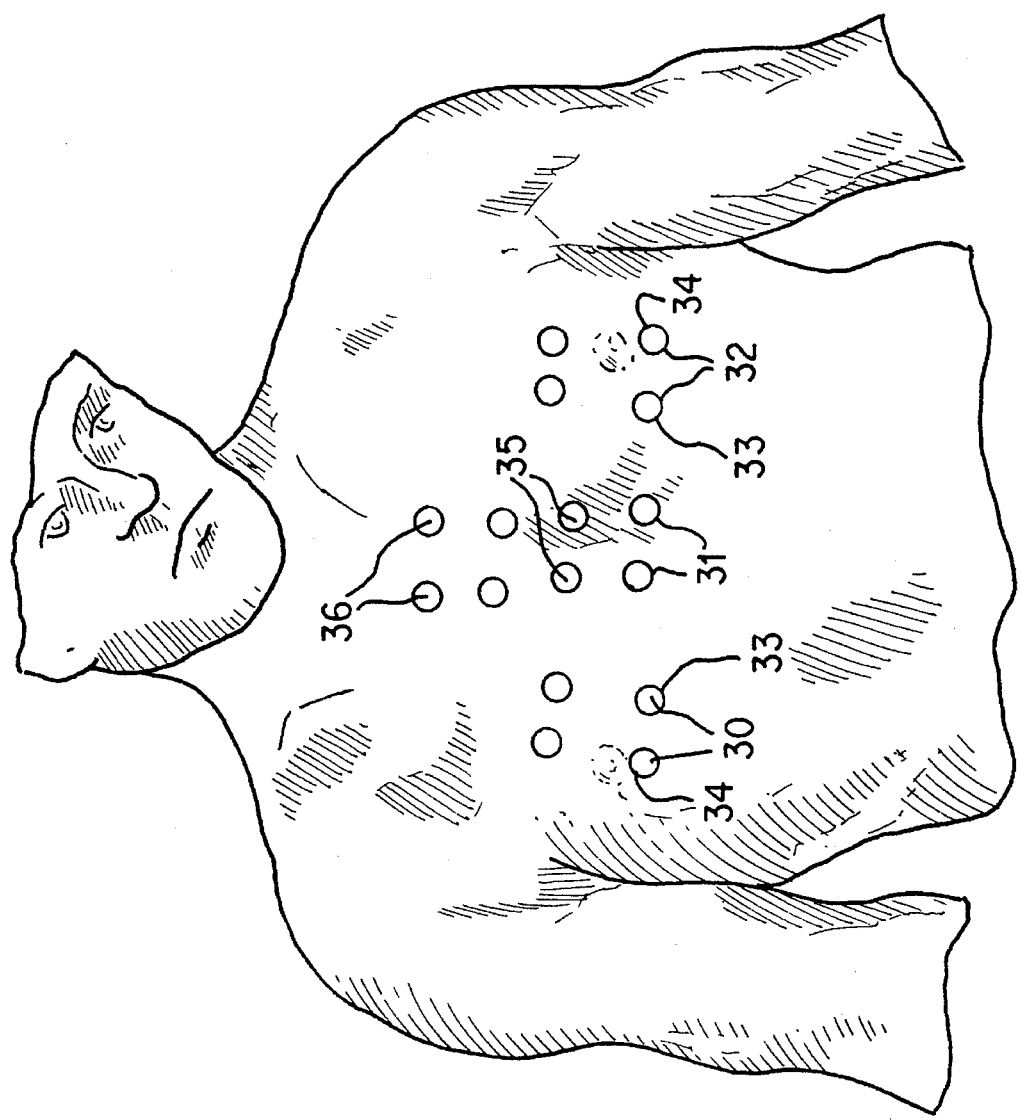
FIG. 3 shows one possible pattern of the placement of pairs of external electrodes, each pair constituting an impedance sensor, on the chest of the patient.

FIG. 3 shows a further embodiment of the present invention where several external pairs 30, 31, 32, 33, 34, 35, 36, of electrodes are attached to the skin of the patient for non-invasive recording of gastroesophageal reflux. Each such pair of electrodes can be used to sense impedance between the pair, and together each such pair constitutes an impedance sensor. Said sensors are connected to an multi-channel MicroDigitrapper™ recorder (European patent number 88/850,292.9) for measuring and recording impedance around and at different levels of the esophagus. Each pair of electrodes over the esophagus will sense changes of impedance in the esophagus directly under that pair. Hence in a reflux situation, pair 31 would detect a change of impedance before the higher pair 35. In the case of swallowed saliva, pair 36 would detect an impedance change before the lower pair 35, which would detect the change before the still lower pair 31. Hence, this embodiment can distinguish between alkaline reflux, which goes up, and swallowed saliva, which goes down, regardless of the pH of the reflux, in much the same manner as discussed above regarding the additional rings 14 and 15. In an alternative placement pattern of electrodes, the individual electrodes are placed around the body at the level of the esophagus. Impedance may then be measured between any pairing of electrodes, and electrode pairs with the esophagus in between are especially significant locations.

The embodiments illustrated and discussed in this specification are intended only to teach those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

For example, other embodiments of the catheter in accordance with the present invention may include rings of conductive material other than gold, and more rings for measurement of impedance in more locations simultaneously. Also, the catheter 2 may use additional sensors commonly used by themselves for esophageal measurements, such as a pH sensor 51, or a pressure sensor 52, communicating with connector 9 by electric wires 61 and 62 respectively. This latter embodiment would allow conventional esophageal catheters, such as pH and pressure catheters, to be modified to simultaneously record and monitor alkaline reflux. Also, a water perfusion pressure sensor could be used in place of an electrical pressure sensor 52.

As a further example, a wide variety of placement patterns can be used for the external electrode placement, as shown in one embodiment in FIG. 3. Likewise, the exact locations of the placement of the impedance sensors, the other biosensors, and the catheter, can be varied in the esophagus and stomach.

I claim:

1. A system for monitoring gastroesophageal reflux comprising:

(a) an electrical connector, (b) a gastroesophageal catheter with a distal end and a proximal end, with an impedance sensor attached to the catheter near the distal end and electrically communicating with said electrical connector at the proximal end, (c) an ambulatory recorder connected to said electrical connector adapted to record impedance data generated by said impedance sensor and communicated to the recorder through said connector, and (d) executable software, resident in the recorder, adapted to determine a presence of gastroesophageal reflux from said impedance data and graphically project said impedance data generated by said impedance sensor and communicated to said recorder through said connector.

2. The system defined in claim 1, further comprising:

an output device for the data recorded in the recorder, the output device being one of (1) a display on the recorder, (2) a printer electrically connected to the recorder, (3) a modem electrically connected to the recorder, and (4) a connector electrically connected to the recorder.

3. The system defined in claim 2, wherein said impedance sensor is a first sensor and further comprising a second impedance sensor attached to the catheter, near the first sensor but closer to the proximal end of the catheter than the first sensor, said second sensor electrically communicating with the electrical connector, said software further adapted to analyze and graphically project impedance data generated by said second sensor and communicated to said recorder through said connector, said recorder further adapted to record impedance data generated by said second sensor and communicated through said connector.

4. The system defined in claim 3, wherein each of the first sensor and the second sensor includes a pair of gold rings encircling an outer surface of the catheter, about 2 mm apart, and further comprising a wire electrically communicating each gold ring to the electrical connector, the first sensor being separated from the second sensor by about 1 cm, said recorder being adapted to record impedance data generated by the gold rings and communicated through said electrical connector, said software being further adapted to analyze and graphically project impedance data generated by each of said first sensor and said second sensor and communicated to said recorder through said connector.

5. The system defined in claim 3, wherein each of said first sensor and said second sensor includes a pair of gold rings encircling an outer surface of the catheter, about 2 mm, apart, and a single gold ring, encircling the outer surface of the catheter, about 2 mm closer to the proximal end of the catheter than said first sensor, electrically communicating with said electrical connector through a wire, and adapted to act variously as a pair with the one of the pair of gold rings and the other of the pair of gold rings of one of said first sensor and said second sensor.

6. The system defined in claim 1, further comprising:

(a) a pH sensor attached near the distal end of the catheter, electrically communicating pH signals to the electrical connector, the recorder further adapted to record the pH signals, and the software further adapted to analyze and graphically project the pH signals, and (b) a pressure sensor attached near the distal end of the catheter, electrically communicating pressure signals to the electrical connector, the recorder further adapted to record the pressure signals, and the software further adapted to analyze and graphically project the pressure signals.

7. A system for monitoring gastroesophageal reflux comprising:

(a) a gastroesophageal catheter with a distal end and a proximal end, (b) an electrical connector at the proximal end of the catheter, (c) a first impedance sensor attached to the catheter near the distal end, said sensor electrically communicating with the electrical connector, said sensor further comprising a pair of gold rings encircling an outer surface of the catheter, about 2 mm apart, each gold ring electrically communicating with the electrical connector through a wire, (d) a second impedance sensor attached to the catheter, near the first sensor but closer to the proximal end of the catheter than the first sensor, said second sensor electrically communicating with the electrical connector, the second sensor comprising a pair of gold rings encircling the outer surface of the catheter, about 2 mm apart, each gold ring electrically communicating with the electrical connector through a wire, the first sensor being separated from the second sensor by about 1 cm, (e) an ambulatory recorder connected to said electrical connector adapted to record impedance data generated by said sensors and communicated through said connector, (f) executable software, resident in the recorder, adapted to determine a presence of gastroesophageal reflux from said impedance data and graphically project impedance data generated by said sensors and communicated to said recorder through said connector, (g) an output device for the data recorded in the recorder, the output device being one of (1) a display on the recorder, (2) a printer electrically connected to the recorder, (3) a modem electrically connected to the recorder, and (4) a connector electrically connected to the recorder, (h) a single gold ring, encircling the outer surface of the catheter, about 2 mm closer to the proximal end of the catheter than said first sensor, and electrically communicating to said electrical connector through a wire, and adapted to act variously as a pair with a first ring of the first sensor and a second ring of the first sensor as two alternate configurations of said first sensor, (i) a pH sensor attached near the distal end of the catheter, electrically communicating pH signals to the electrical connector, the recorder further adapted to record the pH signals, and the software further adapted to analyze and graphically project the pH data, and (j) a pressure sensor attached near the distal end of the catheter, electrically communicating pressure signals to the electrical connector, the recorder further adapted to record the pressure signals, and the software further adapted to analyze and graphically project the pressure signals.

8. A method of monitoring gastroesophageal reflux, comprising the steps of:

(a) placing a number of impedance sensors, each sensor adapted to generate electric impedance signals measuring impedance at a location in an esophagus, (b) electrically connecting said sensors to an electrical connector, (c) connecting an ambulatory recorder to the connector, the recorder adapted to record data communicated through the connector, (d) generating the impedance signals with the sensors, the impedance signals generated in a pattern determined by software resident in the recorder, (e) determining a presence of gastroesophageal reflux from said impedance signals (f) communicating the signals to the recorder through the connector, (g) recording the signals with the recorder, (h) analyzing and graphically projecting recorded data using the software resident in the recorder.

9. The method defined in claim 8, further comprising the steps of:

(a) providing the impedance sensors on a gastroesophageal catheter, with a distal end and a proximal end, so that the impedance sensors are near the distal end of the catheter, (b) inserting the impedance sensors and the distal end of the catheter into the esophagus, (c) electrically connecting the impedance sensors to the connector by wires running through the catheter, and (d) disposing the connector at the proximal end of the catheter.

10. The invention in claim 9, further comprising the steps of:

(a) generating pH signals with a pH sensor attached near the distal end of the catheter, electrically communicating the pH signals to the electrical connector, recording the pH signals with the recorder, and analyzing and graphically projecting the pH data using the software, and (b) generating pressure signals with a pressure sensor attached near the distal end of the catheter, electrically communicating the pressure signals to the electrical connector, recording the pressure signals with the recorder, and analyzing and graphically projecting the pressure data using the software.

* * * * *